(12) United States Patent
Schuehle (Née Hoffmann) et al.

(10) Patent No.: US 8,414,553 B2
(45) Date of Patent: *Apr. 9, 2013

(54) DISPOSABLE ABSORBENT ARTICLE WITH MASKING TOPSHEET HAVING ONE OR MORE OPENINGS PROVIDING A PASSAGEWAY TO A VOID SPACE

(75) Inventors: Anja Schuehle (Née Hoffmann), Hofheim/TS (DE); Joerg Mueller, Karben (DE); Heike Opper, Bad Soden (DE); Georg Pescher, Lemgo (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 310 days.

This patent is subject to a terminal disclaimer.

(21) Appl. No.: 12/853,348

(22) Filed: Aug. 10, 2010

(65) Prior Publication Data

US 2010/0312210 A1    Dec. 9, 2010

Related U.S. Application Data

(63) Continuation of application No. 10/703,239, filed on Nov. 7, 2003, now Pat. No. 7,794,440.

(30) Foreign Application Priority Data

Nov. 8, 2002   (EP) ..................................... 02024889

(51) Int. Cl.
   *A61F 13/15*   (2006.01)
   *A61F 13/20*   (2006.01)
(52) U.S. Cl.
   USPC .................................... 604/385.19

(58) Field of Classification Search .................. 604/348, 604/385.01, 385.101, 385.19
See application file for complete search history.

(56) References Cited

U.S. PATENT DOCUMENTS

| | | | |
|---|---|---|---|
| 2,043,325 A | 6/1936 | Jackson | |
| 2,277,043 A | 3/1942 | Cohn | |
| 2,532,029 A | 11/1950 | Medoff | |
| 2,690,749 A | 10/1954 | Nelson | |
| 2,837,095 A | 6/1958 | Stevenson | |
| 3,214,323 A | 10/1965 | Russell et al. | |
| 3,367,333 A | 2/1968 | Scheier | |

(Continued)

FOREIGN PATENT DOCUMENTS

| | | |
|---|---|---|
| EP | 0 286 543 A2 | 10/1988 |
| EP | 0 357 298 A2 | 3/1990 |

(Continued)

OTHER PUBLICATIONS

Material Safety Data Sheet, Ultra Dawn Hand Dishwashing Liquid, Issue Dates Oct. 6, 2008 and Feb. 10, 2008, pp. 1-5.

(Continued)

*Primary Examiner* — Melanie Hand
(74) *Attorney, Agent, or Firm* — Charles R. Matson (57) ABSTRACT

The present invention relates to a disposable absorbent article, such as a diaper, training pants, adult incontinence article, having a specific topsheet with an opening to receive bowel movement waste (BM) and which is such that it masks the waste present underneath said topsheet. The topsheet is air permeable and it has a uniform pore size distribution with small pores only and it has a low surface energy and therefore an alcohol repellency of at least 7, typically at least 9 or even preferably 10.

19 Claims, 2 Drawing Sheets

U.S. PATENT DOCUMENTS

| | | |
|---|---|---|
| 3,447,536 A | 6/1969 | Snyder |
| 3,468,748 A | 9/1969 | Bassett |
| 3,626,943 A | 12/1971 | Worcester |
| 3,848,594 A | 11/1974 | Buell |
| 3,855,046 A | 12/1974 | Hansen et al. |
| 3,860,003 A | 1/1975 | Buell |
| 3,890,973 A | 6/1975 | Davis et al. |
| RE28,483 E | 7/1975 | Ralph |
| 3,918,433 A | 11/1975 | Fuisz |
| 3,929,135 A | 12/1975 | Thompson |
| 4,323,069 A | 4/1982 | Ahr et al. |
| 4,324,246 A | 4/1982 | Mullane et al. |
| 4,333,979 A | 6/1982 | Sciaraffa et al. |
| 4,342,314 A | 8/1982 | Radel et al. |
| 4,411,928 A | 10/1983 | Baldwin |
| 4,463,045 A | 7/1984 | Ahr et al. |
| 4,515,595 A | 5/1985 | Kievit et al. |
| 4,559,051 A | 12/1985 | Hanson |
| 4,573,986 A | 3/1986 | Minetola et al. |
| 4,578,069 A | 3/1986 | Whitehead et al. |
| 4,609,518 A | 9/1986 | Curro et al. |
| 4,610,678 A | 9/1986 | Weisman et al. |
| 4,610,685 A | 9/1986 | Raley |
| 4,629,643 A | 12/1986 | Curro et al. |
| 4,662,875 A | 5/1987 | Hirotsu et al. |
| 4,662,877 A | 5/1987 | Williams |
| 4,673,402 A | 6/1987 | Weisman et al. |
| 4,678,464 A | 7/1987 | Holtman |
| 4,681,577 A | 7/1987 | Stern et al. |
| 4,695,278 A | 9/1987 | Lawson |
| 4,704,116 A | 11/1987 | Enloe |
| RE32,649 E | 4/1988 | Brandt et al. |
| 4,778,459 A | 10/1988 | Fuisz |
| 4,795,454 A | 1/1989 | Dragoo |
| 4,808,178 A | 2/1989 | Aziz et al. |
| 4,834,735 A | 5/1989 | Alemany et al. |
| 4,834,737 A | 5/1989 | Khan |
| 4,846,815 A | 7/1989 | Scripps |
| 4,888,231 A | 12/1989 | Angstadt |
| 4,892,536 A | 1/1990 | DesMarais et al. |
| 4,894,060 A | 1/1990 | Nestegard |
| 4,909,803 A | 3/1990 | Aziz et al. |
| 4,946,527 A | 8/1990 | Battrell |
| 4,963,140 A | 10/1990 | Robertson et al. |
| 4,988,344 A | 1/1991 | Reising |
| 4,988,345 A | 1/1991 | Reising |
| 4,990,147 A | 2/1991 | Freeland |
| 5,062,840 A | 11/1991 | Holt et al. |
| 5,069,677 A | 12/1991 | Sakurai et al. |
| 5,137,537 A | 8/1992 | Herron et al. |
| 5,147,345 A | 9/1992 | Young et al. |
| 5,151,092 A | 9/1992 | Buell et al. |
| 5,156,911 A | 10/1992 | Stewart |
| 5,176,672 A | 1/1993 | Bruemmer et al. |
| 5,192,606 A | 3/1993 | Proxmire et al. |
| 5,209,801 A | 5/1993 | Smith |
| 5,221,274 A | 6/1993 | Buell et al. |
| 5,260,345 A | 11/1993 | DesMarais et al. |
| 5,306,266 A | 4/1994 | Freeland |
| 5,316,836 A | 5/1994 | Heindel et al. |
| 5,322,729 A | 6/1994 | Heeter et al. |
| 5,330,459 A | 7/1994 | Lavon et al. |
| 5,332,897 A | 7/1994 | Stobbe et al. |
| 5,336,545 A | 8/1994 | Morman |
| 5,342,334 A | 8/1994 | Thompson et al. |
| 5,342,338 A | 8/1994 | Roe |
| 5,344,516 A | 9/1994 | Tanji et al. |
| 5,382,400 A | 1/1995 | Pike et al. |
| 5,382,703 A | 1/1995 | Nohr et al. |
| 5,387,207 A | 2/1995 | Dyer et al. |
| 5,387,450 A | 2/1995 | Stewart |
| 5,397,316 A | 3/1995 | LaVon et al. |
| 5,429,632 A | 7/1995 | Tanji et al. |
| 5,439,459 A | 8/1995 | Tanji et al. |
| 5,439,734 A | 8/1995 | Everhart et al. |
| 5,462,541 A | 10/1995 | Bruemmer et al. |
| 5,494,736 A | 2/1996 | Willey et al. |
| 5,514,121 A | 5/1996 | Roe et al. |
| 5,518,801 A | 5/1996 | Chappell et al. |
| 5,520,673 A | 5/1996 | Yarbrough et al. |
| 5,520,674 A | 5/1996 | Lavon et al. |
| 5,536,555 A | 7/1996 | Zelazoski et al. |
| 5,558,655 A | 9/1996 | Jezzi et al. |
| 5,567,478 A | 10/1996 | Houben et al. |
| 5,576,091 A | 11/1996 | Zajaczkowski et al. |
| 5,576,282 A | 11/1996 | Miracle et al. |
| 5,607,760 A | 3/1997 | Roe |
| 5,609,587 A | 3/1997 | Roe |
| 5,611,791 A | 3/1997 | Gorman et al. |
| 5,623,888 A | 4/1997 | Zafiroglu |
| 5,626,222 A | 5/1997 | Aguilera |
| 5,628,097 A | 5/1997 | Benson et al. |
| 5,635,191 A | 6/1997 | Roe et al. |
| H1670 H | 7/1997 | Aziz et al. |
| 5,643,588 A | 7/1997 | Roe et al. |
| 5,648,167 A | 7/1997 | Peck |
| 5,658,639 A | 8/1997 | Curro et al. |
| 5,667,619 A | 9/1997 | Alikhan |
| 5,705,249 A | 1/1998 | Takai et al. |
| 5,707,950 A | 1/1998 | Kasturi et al. |
| 5,728,081 A | 3/1998 | Baer et al. |
| 5,830,203 A | 11/1998 | Suzuki et al. |
| 5,830,604 A | 11/1998 | Singleton et al. |
| 5,853,403 A | 12/1998 | Tanzer et al. |
| 5,858,515 A | 1/1999 | Stokes et al. |
| 5,876,753 A | 3/1999 | Timmons et al. |
| 5,888,591 A | 3/1999 | Gleason et al. |
| 5,902,297 A | 5/1999 | Sauer |
| 5,919,177 A | 7/1999 | Georger et al. |
| 5,922,417 A | 7/1999 | Singleton et al. |
| 5,941,864 A | 8/1999 | Roe |
| 5,989,478 A | 11/1999 | Ouellette et al. |
| 5,990,377 A | 11/1999 | Chen et al. |
| 6,015,936 A | 1/2000 | Takai et al. |
| 6,045,877 A | 4/2000 | Gleason et al. |
| 6,168,583 B1 | 1/2001 | Tanji et al. |
| 6,186,992 B1 | 2/2001 | Roe et al. |
| 6,261,679 B1 | 7/2001 | Chen et al. |
| 6,353,149 B1 | 3/2002 | Stone |
| 6,380,456 B1 | 4/2002 | Goldman |
| 6,395,957 B1 | 5/2002 | Chen et al. |
| 6,413,247 B1 | 7/2002 | Carlucci et al. |
| 6,417,425 B1 | 7/2002 | Whitmore et al. |
| 6,461,430 B1 | 10/2002 | Kwok |
| 6,465,073 B1 | 10/2002 | Morman et al. |
| 6,482,191 B1 | 11/2002 | Roe et al. |
| 6,537,695 B2 | 3/2003 | McLoughlin et al. |
| 6,569,275 B1 | 5/2003 | Popp et al. |
| 6,863,959 B2 | 3/2005 | Welch et al. |
| 7,144,957 B2 | 12/2006 | Funk et al. |
| 7,223,261 B2 | 5/2007 | Mueller et al. |
| 2001/0000795 A1 | 5/2001 | Bolian, II et al. |
| 2002/0029024 A1 | 3/2002 | Furuya et al. |
| 2002/0049419 A1 | 4/2002 | Mizutani et al. |
| 2002/0087136 A1 | 7/2002 | Widlund |
| 2002/0119301 A1 | 8/2002 | Zhang et al. |
| 2002/0119722 A1 | 8/2002 | Welch et al. |
| 2002/0177632 A1 | 11/2002 | Choi |
| 2003/0143376 A1 | 7/2003 | Toyoshima et al. |
| 2003/0171729 A1 | 9/2003 | Kaun et al. |
| 2004/0092900 A1 | 5/2004 | Hoffman et al. |
| 2004/0092902 A1 | 5/2004 | Hoffman et al. |
| 2004/0097895 A1 | 5/2004 | Busam et al. |
| 2004/0162538 A1 | 8/2004 | Mueller et al. |
| 2005/0004541 A1 | 1/2005 | Roberts |
| 2005/0095942 A1 | 5/2005 | Mueller et al. |
| 2005/0177123 A1 | 8/2005 | Catalan |
| 2005/0215965 A1 | 9/2005 | Schmidt et al. |
| 2006/0025744 A1 | 2/2006 | Mishima et al. |
| 2007/0191806 A1 | 8/2007 | Mueller et al. |
| 2007/0197992 A1 | 8/2007 | Martynus et al. |

FOREIGN PATENT DOCUMENTS

| | | |
|---|---|---|
| EP | 0 433 951 A2 | 6/1991 |
| EP | 0 670 154 A2 | 9/1995 |
| EP | 312118 B1 | 2/1996 |
| EP | 0 814 190 A2 | 6/1996 |

| | | |
|---|---|---|
| EP | 0 811 479 A2 | 12/1997 |
| EP | 0 934 736 A1 | 8/1999 |
| EP | 0 953 323 A | 11/1999 |
| EP | 0 978 264 A1 | 2/2000 |
| EP | 1 057 464 A2 | 12/2000 |
| EP | 1 106 152 A | 6/2001 |
| EP | 1 184 020 A2 | 3/2002 |
| EP | 1 190 690 A2 | 3/2002 |
| EP | 1 201 212 A | 5/2002 |
| EP | 1 279 388 A1 | 1/2003 |
| EP | 1 403 419 A | 3/2004 |
| GB | 2016929 A | 3/1979 |
| GB | 2 284 550 A | 6/1995 |
| GB | 2 287 888 A | 10/1995 |
| GB | 2 288 412 A | 10/1995 |
| GB | 2 297 473 A | 8/1996 |
| GB | 2 328 158 A | 2/1999 |
| GB | 2 329 842 A | 4/1999 |
| JP | H07-136211 | 5/1995 |
| JP | 2002-186645 | 7/2002 |
| JP | 2002-200112 | 7/2002 |
| WO | WO 93/01780 A1 | 2/1993 |
| WO | WO 93/16669 A1 | 9/1993 |
| WO | WO 95/09261 A1 | 4/1995 |
| WO | WO 95/24173 A2 | 9/1995 |
| WO | WO 96/00549 A1 | 1/1996 |
| WO | WO 96/03501 A1 | 2/1996 |
| WO | WO 99/02395 | 2/1996 |
| WO | WO 96/06966 A1 | 3/1996 |
| WO | WO 96/13989 A1 | 5/1996 |
| WO | WO 97/32554 | 9/1997 |
| WO | WO 98/08476 A1 | 3/1998 |
| WO | WO 98/43587 A1 | 10/1998 |
| WO | WO 98/56326 A1 | 12/1998 |
| WO | WO 99/02393 | 1/1999 |
| WO | WO 99/30661 A1 | 6/1999 |
| WO | WO 99/56680 A1 | 11/1999 |
| WO | WO 99/62446 A1 | 12/1999 |
| WO | WO 00/01334 A1 | 1/2000 |
| WO | WO 01/00053 A1 | 1/2001 |
| WO | WO 01/06974 A1 | 2/2001 |
| WO | WO 01/66058 A1 | 9/2001 |
| WO | WO 02/34186 A1 | 5/2002 |
| WO | WO 02/48440 A2 | 6/2002 |
| WO | WO 03/009795 | 2/2003 |
| WO | WO 2006/031639 A1 | 3/2006 |

OTHER PUBLICATIONS

INDA Standard Test: IST 80.6 (95), Association of the Nonwoven Fabrics Industry, Standard Test Method for Alcohol Repellency of Nonwoven Fabrics, pp. 73-74, 1995.

ASTM Designation: F316, Standard Test Method for Pore Size Characteristics of Membrane Filters for Use With Aerospace Fluids, pp. 707-713, 1980.

DISPOSABLE ABSORBENT ARTICLE WITH MASKING TOPSHEET HAVING ONE OR MORE OPENINGS PROVIDING A PASSAGEWAY TO A VOID SPACE

CROSS REFERENCE TO RELATED APPLICATION

This application is a continuation of U.S. application Ser. No. 10/703,239 filed Nov. 7, 2003, which claims priority to European Patent Application No. EP 02024889.4, filed Nov. 8, 2002, U.S. application Ser. No. 10/703,239 is incorporated by reference herein.

FIELD OF THE INVENTION

This invention is directed to disposable absorbent articles, such as diapers, training pants, adult incontinence articles, feminine protection articles and the like having a specific topsheet with an opening to receive viscous bodily waste, e.g. bowel movement waste (hereinafter referred to as BM) and which is such that it masks the waste present underneath said topsheet.

BACKGROUND OF THE INVENTION

In the last decade, there has been much research on diaper topsheets that have an opening, which leads to a void space to receive or store BM. The focus has mainly been to improve the positioning of the opening against the wearer's body and in proximity of the anus of the wearer, for example by use of elastication means around the opening in the topsheet.

Many types of materials have been suggested as topsheet, including both hydrophobic and hydrophilic topsheets, such as for example described in U.S. Pat. No. 4,662,877 and U.S. Pat. No. 4,990,147.

The inventors have now found that it is highly desirable that the BM, once received through the opening, is not visible for the person changing the article, i.e. that the topsheets masks the BM. The topsheet further has to be such that it has a high air-permeability, and that it is flexible and not too thick, in order to provide comfort to the wearer. The various hydrophilic and hydrophobic topsheet materials suggested in the art do not provide such masking. Other materials used in parts of a diaper that may mask BM, such as a materials generally used as backsheets, are too thick or not air permeable enough to be used as comfortable topsheet.

The invention thus seeks to develop a diaper, which has a topsheet with one or more opening, which is such that it masks the BM received through the opening (s) and present underneath it.

The inventors found that this can be effectively achieved by using in an absorbent article a topsheet with a uniform and small pore size distribution and at least and an inner surface (i.e. facing the backsheet) that has a very low surface energy. Surprisingly and unexpectedly, the combination of these properties provides excellent masking of the BM, whilst the use of either one of the properties alone, does not provide the required masking benefit.

The preferred topsheet of the diapers of the invention ensures that the appearance of at least the inner surface of the topsheet remains about the same before and after contact with BM, e.g. a white, non-transparent topsheet remains like that with BM underneath and in contact with it. Thereby, the BM is effectively hidden for the person changing the diaper.

Surprisingly, the inventors have found that the use of this topsheet of the diapers of the invention, which has a very low surface energy and a uniform porosity, also helps reduce the leakage of BM, and in particular very runny BM, from the void space underneath the topsheet, back through and onto the topsheet and to the wearer's skin. This has thus also been found to be a highly effective way to reduce leakage from the diaper. Also, the topsheet of the diapers of the invention provide an effective rewet barrier for runny BMs and therefore protect the skin from BM and the irritants in it.

It should be noted that it is known in the art to apply chemicals to a topsheet of a diaper to make it more hydrophobic or hydrophilic, for example to control urine absorption or repellency, but it has not been recognized in the art that it is beneficial to significantly reduce the surface energy of the topsheets with one or more large opening, to aid the masking of BM in the diaper and to reduce leakage. Also, it has not been realized that the combination of a very low surface energy and a uniform pore size distribution is required to provide masking of BM received in the diaper.

SUMMARY OF THE INVENTION

The invention provides in a first embodiment a disposable absorbent article like a diaper, training pants, adult incontinence article or sanitary napkin, with a backsheet, which in use faces the garment of the wearer, and a topsheet, which has an inner surface, facing the backsheet and an outer surface, facing in use the wearer's body, said topsheet having one or more openings that provide a passageway to a void space for receiving bodily exudates therein, positioned between the topsheet and the backsheet, whereby said topsheet comprises at least one sheet of fibrous material with a uniform pore distribution, as defined herein, and said topsheet has an air permeability of at least 3 Darcy/mm, more preferably at least 5 Darcy/mm and most preferably at least 10 Darcy/mm or even more preferably at least 20 Darcy/mm or even more preferably at least 30 Darcy/mm, and the topsheet (e.g. its inner surface at least) has an mean alcohol repellency of at least 7, preferred of at least 8, more preferred of at least 9 and most preferred even 10. Most preferred materials with an alcohol repellence of at least 10 generally have a surface energy of less than 25 mN/m and contact angles with water of above 130 deg.

In another embodiment of the invention, a disposable absorbent article is provided which has a backsheet, a topsheet with an opening as above, whereby said topsheet has an air-permeability of at least 3 Darcy/mm, more preferably at least 5 Darcy/mm and most preferably at least 10 Darcy/mm or even more preferably at least 20 Darcy/mm or even more preferably at least 30 Darcy/mm, and said topsheet (e.g. at least its inners surface) has a rewet value of less than 4.5 g, preferably less than 3.5 g even more preferred less than 2.5 g and most preferred less than 1.5 g.

DETAILED DESCRIPTION OF THE INVENTION

As used herein, the following terms have the following meanings:

'Absorbent article' refers to wearable devices, which absorb and/or contain liquid, and more specifically, refers to devices, which are placed against or in proximity to the body of the wearer to absorb and contain the various exudates discharged from the body.

'Longitudinal' is a direction running parallel to the maximum linear dimension, typically the longitudinal axis, of the article and includes directions within 45° of the longitudinal direction. 'Length' of the article or component thereof, when used herein, generally refers to the size/distance of the maximum linear dimension, or typically to the size/distance of the longitudinal axis, of an article or part thereof.

The 'lateral' or 'transverse' direction is orthogonal to the longitudinal direction, e.g. in the same plan of the majority of the article and the longitudinal axis, and the transverse direction is parallel to the transverse axis. 'Width' of the article or of a component thereof, when used herein, refers to the size/distance of the dimension orthogonal to the longitudinal direction of the article or component thereof, e.g. orthogonal to the length of the article or component thereof, and typically it refers to the distance/size of the dimension parallel of the transverse axis of the article or component.

The 'Z-direction' is orthogonal to both the longitudinal and transverse directions, e.g. running parallel to the minimum linear dimension of the article. 'Thickness' or 'caliper' of the article or component thereof, when used herein, refers to the size/distance of the z-direction dimension.

As used herein, the term "void space" is a cavity sized to accept and contain bodily exudates such as fecal material, present in at least the relaxed sate of the article.

As used herein, 'elasticated' and 'elasticated topsheet' means, that the item or the topsheet comprises at least a portion made of elastic material, which is elastic in at least the longitudinal direction, including the situation that the topsheet as a whole is of elastic materials (elastically extendible in longitudinal direction) and/or that the topsheet contains elastic bands or strands, elastically extendible in longitudinal direction.

The invention is equally applicable to absorbent articles such as pull-on or training pants, pant-type diapers, incontinence briefs, incontinence undergarments, absorbent inserts, diaper holders and liners, feminine hygiene garments, bandages and the like, however, a preferred embodiment of an absorbent article of the present invention is a pull-on or training pants or diaper, preferably a diaper shown and described hereinafter. Thus, whilst the invention is described in detail with reference to a (baby, infant or adult) diaper, this description is equally applicable to other wearable disposable article.

The disposable, wearable absorbent article, e.g. diaper, of the invention has a backsheet, which is typically liquid impervious, but preferably breathable or even moisture-vapor permeable. Any material known to be suitable as backsheet can be used herein. Materials known in the art to be useful as backsheet material have a air permeability up to about 0.2 Darcy/mm. The backsheet, or any portion thereof, may be elastically extensible in one or more directions. In one embodiment, the backsheet may comprise a structural elastic-like film ("SELF") web, A structural elastic-like film web is an extensible material that exhibits an elastic-like behavior in the direction of elongation without the use of added elastic materials. The SELF web includes a strainable network having at least two contiguous, distinct, and dissimilar regions. SELF webs suitable for the present invention are more completely described in U.S. Pat. No. 5,518,801.

Typically, also an absorbent core is present, which is preferably positioned between at least a portion of the topsheet and the backsheet.

The absorbent core that is preferably present, may comprise any absorbent material which is generally compressible, conformable, non-irritating to the wearer's skin, and capable of absorbing and retaining liquids such as urine and other certain body exudates, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; super absorbent polymers; absorbent gelling materials; or any other known absorbent material or combinations of materials. Exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147; U.S. Pat. No. 5,260,345; U.S. Pat. No. 5,387,207; and U.S. Pat. No. 5,625,222.

The article, e.g. diaper, of the invention may have side panels, and/or more preferably one or more leg cuffs that provide improved containment of liquids and other body exudates. Leg cuffs may also be referred to as leg bands, side flaps, barrier cuffs, or elastic cuffs, as described in; U.S. Pat. No. 3,860,003; U.S. Pat. Nos. 4,808,178 and 4,909; U.S. Pat. Nos. 4,695,278 and 4,795,454.

The diaper typically has a first or front waist region a second or back waist region, opposed to the first waist region, and a crotch region, located between the first waist region and the second waist region. The crotch region is typically that portion of the diaper which, when worn, is between the legs of the wearer. The waist regions of the diaper, when worn, typically gather or encircle the waist of the wearer and are generally at the highest at the highest elevation of the article, when the wearer is in the standing, upright position. The waist region, or preferably the waistband typically comprises the force line of the diaper.

Typically, the waist regions of the diaper have a portion, which is or forms the waistband. In one type of diapers, the waistband is open prior to use and needs fastening around the waist of the wearer. Thereto, the diaper preferably has a fastening system, typically joined to the waist region or band. The fastening system preferably maintains the first waist region and the second waist region in a touching or overlapping configuration so as to provide lateral tensions or force line about the circumference of the diaper to hold the diaper on the wearer. The fastening system preferably comprises tape tabs and/or hook and loop fastening tabs, although any other known fastening means are generally acceptable. Some exemplary fastening systems are disclosed in U.S. Pat. No. 3,848,594; U.S. Pat. No. 4,662,875; U.S. Pat. No. 4,846,815; U.S. Pat. No. 4,894,060; U.S. Pat. No. 4,946,527; U.S. Pat. No. 5,151,092; and U.S. Pat. No. 5,221,274; and U.S. Pat. No. 4,963,140.

In alternative embodiments, the article is to be used as a pull-on type diaper, such as a training pant. Then, typically, the opposing sides of the garment may be seamed or welded to form a pant, such that the front waist portion or waistband and a back waist portion or waist band are (irremovably) connected prior to use, by a first connection area and a second connection area.

The waist regions may comprise an elastic waist feature. Such an elastic waist feature may be constructed in a number of different configurations including those described in U.S. Pat. No. 4,515,595; U.S. Pat. No. 5,151,092.

The backsheet may be attached or joined to the topsheet, the absorbent core, or any other element of the diaper by any attachment means known in the art. It may be highly preferred that the edges of the topsheet and backsheet are directly attached to one another, but that the longitudinal edges of the topsheet and the core are not attached to one another, or optionally only partially attached. The attachment means may for example include a uniform continuous layer of adhesive, a patterned layer of adhesive, or an array of separate lines, spirals, or spots of adhesive, such as disclosed in U.S. Pat. No. 4,573,986. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Preferred may be that the article, e.g. the diaper, includes a topical agent for the skin of the wearer, preferably on the elasticated leg cuffs, when present and/or around the opening of the topsheet, in particular when the edges of the opening is elasticated, as described herein. Preferred agents include powders and lotions; preferably talc and/or wax, as generally known in the art. It has been found to be very useful to apply such an agent, in particular talc or wax to the elastics around the opening in the topsheet, to reduce pressure marks of the elastics on the skin of the wearer.

The article may also comprise a topical adhesive or body adhering composition that acts to hold the diaper or the topsheet or the opening further in place during use. In one preferred embodiment, the topical adhesive is present on the elasticated regions along the edges of the opening. Suitable body adhesives are known in the art.

Topsheet

The topsheet of the article of the invention is air-permeable. This is important to ensure comfortable wear to the user and to reduce the risk of skin problems. The topsheet typically has an air permeability of at least 3 Darcy/mm, more preferably at least 5 Darcy/mm and most preferably at least 10 or even at least 20 or even at least 30 Darcy/. This can for example be determined by the method set out below.

The inventors have found than BM mixed with urine can have very low surface tension, e.g. of about 25 to 30 mN/m. Therefore the topsheet has a very low surface energy, reflected by a very high alcohol repellency value.

The mean alcohol repellency of the topsheet is at least 7.0, preferred at least 8.0 more preferred at least 9.0 and most preferred the topsheet has an alcohol repellency of 10.

The surface energy of the topsheet or part thereof, e.g. the inner surface of the topsheet, is less than 28 mN/m or preferably less than 24 mN/m and more preferably less than 20 nN/m.

The topsheet preferably is at least partially treated with a chemical, which lowers the surface energy of the topsheet, to thus helps to provide the required masking, herein referred to as masking facilitating agent.

To obtain topsheets with low surface energy, i.e. high alcohol repellency, one can use any method of applying the above-mentioned masking facilitating agents.

The method of applying the masking facilitating agent should preferably be such that a very thin coating of agent is deposited on the topsheet or part thereof, and it should be such that the air permeability and porosity is substantially unchanged.

Preferred is to topically apply the masking facilitating agent to a fibrous web or to add the masking facilitating agent in molten state to the compound (s) used to make the topsheet, e.g. to the fibers, prior to formation of the topsheet web. Thus for example, if the topsheet is a non-woven material made of a fiber blend, this fiber blend can comprise a masking facilitating agent in molten state, that will provide the resulting non-woven with a high alcohol repellency and a low surface energy. The use of one or more melt-in masking facilitating agents may be combined with topical treatment with one or more masking facilitating agent, as mentioned above.

Useful agent include fluorocarbons as described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000. Other agents include silicone. Useful methods for applying the agent to the topsheet, without reducing the air permeability, can be found in U.S. Pat. No. 5,322,729 and PCT Publication WO 96/03501.

Preferred agents may be selected from the group comprising fluorocarbons, siloxanes, polysiloxanes, preferably including fluorinated monomers and fluorinated polymers, including hexafluoroethylene, hexafluoropropylene and vinyl fluoride and vinylidene fluoride, fluoroacrylate and fluoromethacrylate. Highly preferred is that the topsheet is provided with poly (tetra) fluoroethylene, fluorinated ethylene-propylene copolymers and/or fluorinated ethylene-tetrafluoroethylene copolymers masking facilitating agent.

The masking facilitating agent is most effectively applied to fibrous non-woven web, which comprising thermoplastic polymer fibers, preferably selected from the group comprising: polyolefins, polyesters, polyurethanes, and polyamides, most preferably the thermoplastic polymer being a polyolefin, most preferably being polypropylene or polyethylene.

In addition to the high alcohol repellency, the topsheet also has a uniform pore size distribution with small pores, i.e. the topsheet has pores with a maximum pore size (bubble point diameter) of less than 100 μm preferably less than 75 μm more preferable less than 50 μm and most preferably less than 25 μm. This can be determined by the method set out hereinafter.

The pores of the topsheet are preferably also such that the mean pore size is less than 29 μm, preferred less than 17 μm more preferred less than 13 μm and most preferred less than 10 μm.

The topsheets of the articles of the invention, with high alcohol repellency as well as small uniformly distributed pores, also help to reduce the contamination of the skin with runny BM. This can be characterized with the BM rewet method, as set out herein.

In one embodiment of the invention, the BM rewet of the topsheets is less than 4.5 g, preferably below 3.5 g more preferably below 2.5 g and most preferably below 1.5 g.

It may be that the topsheet comprises more than one sheets or web, whereby only one sheet or web has this low surface energy, provided the inner surface of the topsheet experiences this low surface energy. The webs or sheets may be carded webs, but preferably the topsheet comprises a spunbond and/or meltblown non-woven web(s).

It may be preferred that the topsheet is a laminate of two or more sheets or webs, whereby preferably one or more of the webs is treated with one or more of the agents described above, to have a low surface energy.

The topsheet herein comprises preferably at least two layers one of which is a meltblown (M) layer and another is either a spunbond (S) or a carded (C) layer.

Preferred executions are SM SMS, SMMS, SSMS, SSMSS, SSMMS, CM or CMC non-wovens laminates, preferably one web being treated with a masking facilitating agent.

Preferred is a laminate whereby the inner web (facing the backsheet of the article) and/or a middle web is such that the (inner surface of the) topsheet will have a low surface energy, as defined herein. For example, it is highly preferred that the topsheet comprises aSMS laminate, whereby at least the meltblown web is treated such as to provide the low surface energy of the inner surface (and preferably also the outer surface) of the topsheet.

Preferably the carded and non-woven webs are formed from polyethylene, polypropylene and/or polybutylene polymer fibers, or (a mixture of) fibers of a copolymers of polyethylene, polypropylene and/or polybutylene; most preferred are polypropylene polymer fibers.

The topsheet is preferably very thin, soft and compliant; it preferably has a very low basis weight, preferably less than 35 g/m², or even less than 25 g/m², or even less than 15 g/m². It preferably has a caliper or thickness of less than 0.2 mm, or even less than 0.15 mm, or even less than 0.1 mm.

Preferred materials used for the topsheet herein are for example are for example a 34 gsm SMS polypropylene non-woven laminates treated with Dipolit, having a maximum pore size (pore size) of 32 μm, an airpermeability of 34 Darcy/mm, and an alcohol repellency of 10 and a rewet of 2.8, as for example available from Pegas under the name Pegaphob 02 445 032; a 24 gsm SSMMSS polypropylene non-woven laminates treated with Dipolit, having a maximum pore size of 57 μm, an air permeability of 52 Darcy/mm, and an alcohol repellency of 10 and a rewet of 2.9, for example available from Pegas under the name Pegaphob 02 445 024; a 34 gsm SSMMS polypropylene non-woven laminates treated with Dipolit, having a maximum pore size of 48 μm, an air permeability of 42 Darcy/mm, and an alcohol repellency of 10 and a rewet of 3.0, for example available from Pegas under the name Pegaphob 02 445 032; a 20 gsm web available from Sandler under the code VP21/00/75, having a maximum pore size of 22 μm, an air permeability of 48 Darcy/mm, and an alcohol repellency of 9 and a rewet of 1.7; a 10 gsm web available from Sandler under the code VP21/00/76, having a maximum pore size of 36 μm, an air permeability of 95 Darcy/mm, and an alcohol repellency of 10 and a rewet of 2.1; a 20 gsm web available from Sandler under the code VP21/00/76, having a maximum pore size of 23 μm, an air permeability of 35 Darcy/mm, and an alcohol repellency of 10 and a rewet of 1.1, the latter being most preferred.

Another embodiment of the invention is a disposable absorbent article with a topsheet formed from a film with slated cone-shaped pores, which are positioned in the topsheet under an angle with the z-axis of the topsheet (i.e. thus not perpendicular to the plane of the topsheet), and which under pressure can move into a position which is more parallel to the plane of the topsheet (more parallel to transverse or longitudinal axis). This type of porous topsheet material also provides masking and reduced leakage when in use pressure is applied to it; this typically occurs in use when the present BM or the movement of the user increases the pressure against it. The slated cone films preferably also have the alcohol repellency values, air permeability, rewet value and/or pore size distribution as mentioned above. As for the materials described above, they slanted cone topsheet preferably has pores which have an mean pore size of less than 20 μm, preferred less than 17, more preferred less than 14 and most preferred less than 10 μm.

Suitable materials are three-dimensionally formed slanted cones films, as described in PCT applications US99/02395 or US99/02393, both filed on Feb. 3, 1999. Such films may be combined with for example a support sheet, such as a non-woven web, to form laminates. The support sheet, e.g. non-woven web, can be attached to the slanted cone film over the full area, but preferably the layers are only attached to each other in the peripheral regions of the layers. A preferred three-dimensional formed film with slanted cones is available from Tredegar under the designation V174 LD40.

The topsheet of the article of the invention has an opening, preferably an elongated split opening, leading to a void space. The dimensions of the opening may vary, depending for example on the size of the topsheet and/or the article. The opening may extend over the full length of the topsheet. Preferred may be, in particular for size 4 diapers, that the length of the opening, e.g. in relaxed state is preferably from 5 to 30 cm, or even from 10 to 25 cm, or even from 12 to 20 cm. The width of the opening of such articles, e.g. in a relaxed state, is preferably from 2 to 10 cm, more preferably 3 to 8 cm.

In the fully stretched state, the length of the opening may preferably be from 20 to 35 cm, and the width may preferably be from 3 to 6 cm.

The topsheet has preferably elasticated regions, which are preferably positioned along the two longitudinal edges of the opening (so that each edge has at least one elasticated region), extending from said opening towards the first (front) and second (back) waist region, preferably such that the end portions of the elastic regions can be attached or joined to the waist region. Thus, the elasticated regions are preferably longer than the opening, both in relaxed as in stretched state. Preferred is that the elastic region is positioned over the full length of the active topsheet, e.g. the part of the topsheet which in use is intended to receive body exudates, typically the topsheet minus the parts thereof which form (part of) the waist region or band.

The length of the elastic region will typically depend on the size of the topsheet and/or the article. For example, for a size 4 diaper, the length of the elastic region in relaxed position may be 10 to 30 cm, or even 15 to 25, whilst in stretched position preferably from 20 to 60 or even 25 to 45 or even 30 to 40 cm.

The elastic region may be in the form of two or more substantially parallel elasticated zones, and preferred is that the elasticated regions are shaped such that the middle portions of the regions are substantially parallel to one another, whist the end portions (at least in relaxed state) bend away from one another (in the plane of the topsheet), so that the distance between the end portions of the elastic regions is larger that the distance between the middle portions of the elastic regions. Then, the end portions of the elasticated regions make typically each an angle with the longitudinal axis of the opening, preferably each angle being between 20° and 30°, and preferably such that the angle between the end portions is about twice as much, e.g. between 40° and 60°. This is herein referred to as an X-shape.

Preferred is that, when in relaxed state, the elastic regions or part thereof are under an angle with the adjacent topsheet, such that the elastic regions are (also) bending out of plane of the topsheet, bending upwards and away from the void space (under the topsheet).

A preferred process that can be reapplied to make the diaper of the invention is for example described in EP-A-1201212.

Highly preferred is that the article (e.g. diaper or training pants) of the invention comprises an additional sheet, which serves to immobilize BM, and which is located underneath the topsheet, i.e. between the topsheet and the backsheet, or between the topsheet and the absorbent core, which is typically present.

The additional sheet is preferably made of at least a fibrous web (sheet) which has regions were the fibers are bonded and regions where the fibers are unbonded, so-called bonded and unbonded regions, respectively. The fibers extend from one bonded region through an unbonded region to another bonded region, typically so that the fibers form loops from one bonded region to the next. The bonded regions are such that they form the support structure for the unbonded regions, so that no backing support layer is necessary. The additional sheet is typically a single or unitary sheet or web.

Preferably, the fibers running from the same bonded region to the next same bonded region are about parallel to another. Preferably, the bonded regions are in one plane, e.g. to form a planar support structure, and the fibers extend upward and downward out of the plane formed by the bonded region support structure, preferably in the form of loops.

The bonded regions can be in any form, provided said support structure for the unbonded regions is created. For example, a bonded region can be in the form of a dot, square, rectangle, circle, triangle, or line. A number of bonded regions can also be such that they together form a line of not connected dots, squares, lines or strips etc. In the latter case, the bonded regions should be close enough together to ensure that sufficient bonding is achieved to provide the support structure for the unbonded regions.

The unbonded regions may also for example be circular or round, square, rectangular, triangular, diamond-shaped, or hexagonal and/or oval.

Preferably the (largest convex) surface area within the unbonded region is at least 2 $mm^{2'}$ preferably at least 5 $mm^2$ or even at least 10 mm2, or even at least 20 $mm^2$ or even at least 25 $mm^2$, or even at least 30 $mm^2$, and typically up to 200 $mm^2$, or even up to only 100 $mm^2$.

The bonded regions have a certain width dimension, which is, when used herein, the smallest distance between two opposing sides of a bonded regions, in the plane which the bonded regions support structure forms (i.e. thus not the thickness dimension of the bonded regions. Typically, this width dimension is less than 3 mm, or even less than 2 mm, or even less than 1 mm, or even less than 0.8 mm, or even less than 0.5 mm.

The total surface area relationship between the total surface area of the unbonded regions and of the bonded regions is preferably: 20:1, or even 15:1, or even 10:1; or even 8:1, but preferably more than 2:1, or even more than 3:1.

Preferably, the bonded regions are in the form of lines, whereby preferably each bonded region (line) crosses at least one another bonded region (line). Preferably, the bonded regions are positioned in both longitudinal and transverse direction, preferably parallel to one another in each respective direction, as can be seen in FIG. 4a.

The additional sheet may have any basis weight, but preferably, this is from about 10 to 45 g/$m^2$, or even from 20 to 40 g/$m^2$, or even from 30 to 35 g/$m^2$.

A highly preferred additional sheet comprises or consists of a web with a caliper of about 0.25-0.29, preferably about 0.27 mm, compression resistance of about 40-60%, preferably about 55%, a basis weight of about 28-34 g/$m^2$, preferably about 32 g/$m^2$, with preferably unbonded regions of about 22 $mm^2$ to 30 $mm^2$, preferably about 25 $mm^2$, and bonded regions with a maximum width of 0.7 mm to 1.1 mm, preferably 0.9 mm, in the shape of crossing lines. Highly preferred additional sheets are available from Sandler with the trade name: VP 3001/11-32 gsm.

Test Methods Used Herein:

Air Permeability

The air permeability is determined by measuring the time in which a standard volume of air is drawn through the test specimen at a constant pressure and temperature. This test is particularly suited to materials having relatively high permeability to gases, such as preferred herein, in particular non-woven materials.

A Tex Test FX3300 instrument is used. The Test Method conforms to ASTM D737. The test is operated in a laboratory environment typically about 22±2° C. and about 35%±15% relative humidity. The test specimen has to be conditioned for at least 2 hrs. The test pressure is 125 Pascals and the test area is 38 $cm^2$. In this test, the instrument creates a constant differential pressure across the sample, which draws air through the sample. The rate of air flow through the sample is measured in $ft^3$/min/$ft^2$ and converted to permeance (in Darcy/mm) according to the Darcy's Law:

$$K/d(\text{Darcy/mm}) = (V^*\mu)/(t^*A^*\Delta p)$$

wherein k is the permeability per unit area of the specimen; V/t is the volumetric flow rate in $cm^3$/sec; μ is the viscosity of air (1.86*$10^{-5}$ Pa sec); d is the test material thickness in mm; A is the cross sectional area of the specimen in $cm^2$; Δp is the pressure differential in Pascal or Pa; and 1 Darcy=9.869*$10^{-9}$ $cm^2$.

For each sample, three replicates should be run, and the meant result is reported as air permeability herein.

Alcohol Repellency (Indication for Surface Energy)

The alcohol repellency can be determined by the INDA Standard Test Method IST 80.6 (95), as published in 1996 and available from INDA, NC27513, USA.

This method is used to measure the resistance of a sample to wetting and penetration of alcohol or alcohol/water solution.

The alcohol repellency value of a fabric corresponds to the highest numbered test solution, which does not penetrate the fabric. Thus, as used herein, a topsheet with an alcohol repellency of 7 is such that a test solution of 70% alcohol (anhydrous ethanol) and 30% deionised water does not penetrate through the sample, but a solution of 80% alcohol and 20% water will penetrate through.

Highly preferred herein is a topsheet with an alcohol repellency of 10, whereby neither a 100% alcohol solution nor any of the alcohol/water solutions penetrates though the sample.

Maximum Pore Size, Mean Pore Size and Pore Size Distribution

The maximum pore size and mean pore size, as used herein, can be calculated by use of ASTM method F316-80. As coulter porometer, required in this ASTM method, a porometer as available from PMI can be used.

Rewet Value and Method

The rewet value of at he first or second topsheet of the absorbent article of the invention can be determined by measuring the amount of BM anologue 4A which is transferred from the topsheet to dry pick-up paper under a specific pressure and this is done as follows.

| BM analogue 4A comprises: | |
|---|---|
| Feclone # 2* | 3.86% |
| Feclone # 4* | 3.86% |
| Ultra Dawn** | 0.62% |
| Distilled water | 91.66% |

*available from SiliClone Studio - Doretta L. Erb - Valley Forge, PA 19481, USA.
**detergent sold in the USA by The Procter & Gamble Company.

The BM anologue 4A is prepared as follows:

A quantity of distilled water greater than what is needed to make your analogue is heated to 90° C. in a container. The appropriate amounts of Feclone 2 and 4 above are weighed and transferred to another container and thoroughly blended. Then the Ultra Dawn is mixed in. Then, the water is mixed with the other ingredients to a homogenous blend.

Then, 10 g+/−0.2 g of this BM analogue 4A is put into a petri-dish. A piece of the topsheet (of which the rewet value is to be determined) is placed on top of the petridish, such that the BM analogue and the edges of the petri dish are covered. If the topsheet material has one surface, which is more fuzzy than the other surface, the more fuzzy surface is positioned upwards, away from the BM analogue.

5 plies of dry pick-up paper (10 cm*10 cm; Ahlström Grade 632 or equivalent) are weighed and then placed on top of the topsheet material.

Then, a force of 8 lbs weight is applied on the 10 cm*10 cm surface area (i.e. 0.5 psi, 3543 g per 10 cm*10 cm surface area) for 3 min.

Then, the 5 plies of pick-up paper are weighed again and the weight difference of the pick-up paper is calculated. The increase in weight X is the weight of the adhered or absorbed BM analogue on or in the pick-up paper. Then, the rewet percentage is determined by calculating what percentage X is of the initial 10 grams BM analogue. For example, if the pick-up paper weight is increased by 0.2 gram, then X is 0.2 gram and the percentage rewet or rewet value of the topsheet is: (0.2/10)×100%=2% rewet.

Caliper (Thickness)

This test is to measure the caliper of a web or sheet used in the articles of the invention.

The caliper as referred herein is measured by taking 3 samples of a web or sheet, e.g. about 15 cm$^2$ (1.5×1.5 square inch) each, for example by punching this out of a larger sheet. Then, in 3 separate experiments, the maximum caliper of each sample is measured and an mean is obtained.

In each experiment, a sample is fixed in one position, and then a specific pressure of 0.09 psi (620 Pa) is applied on the sample, and the caliper is measured with a digital caliper gauge. The caliper measurements of a sample are always done at the same spot of that sample.

Preferred Articles of the Figures

A preferred diaper of the invention is now described with reference to FIGS. 1 and 2.

Figure 1:
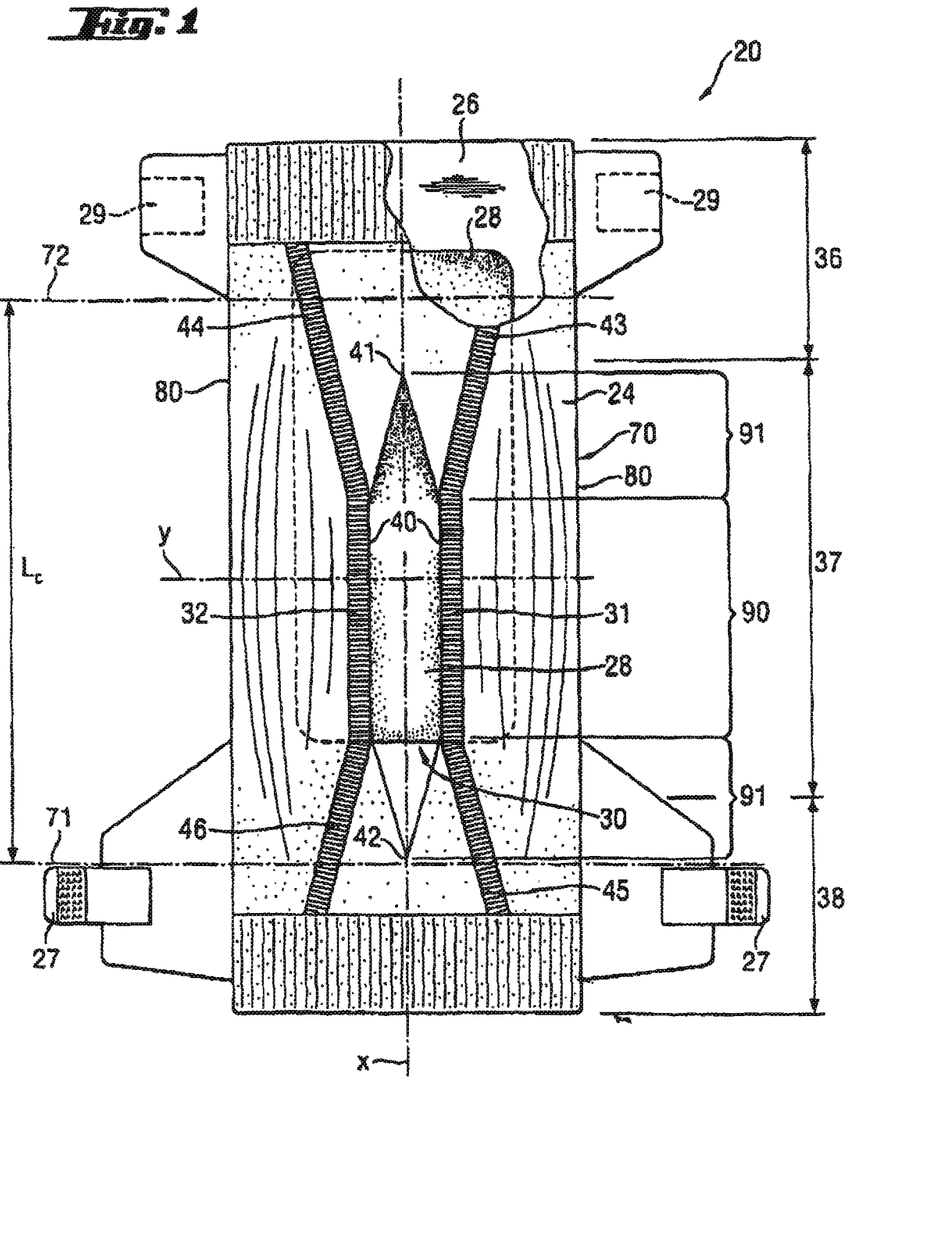
FIG. 1 shows a planar view of a preferred diaper of the invention, and the preferred topsheet 24 thereof.

FIG. 1 is a plan view of the diaper 20 in its stretched state, with portions of the structure being cut away to more clearly show the underlying structure of the diaper 20 and with the portion of the diaper 20 which contacts the wearer facing the viewer. One end portion of the diaper 20 is configured as a first waist region 36 of the diaper 20. The opposite end portion is configured as a second waist region 38 of the diaper 20. An intermediate portion of the diaper 20 is configured as a crotch region 37 that extends longitudinally between the first and second waist regions 36 and 38. The waist regions 36 and 38 generally comprise those waist portions of the diaper 20 which, when worn, encircle the waist of the wearer. The waist regions 36 and 38 includes elements which can gather about the waist of the wearer to provide improved fit and containment, or which typically can gather around the waist and can be fastened around the waist by use of fastening means, such as tabs 27, which are fastened to landing zones 29. The crotch region 37 is that portion of the diaper 20 which, when the diaper 20 is worn, is generally positioned between the legs of the wearer.

The diaper 20 comprises the topsheet 24, a liquid impervious backsheet 26, and an absorbent core 28 encased between the topsheet 24 and the backsheet 26. The topsheet is air permeable, has a uniform pore size with only small pores and has a low surface energy as described above. Preferred are the laminates as available from Pegas or Sandler, described above; preferably, the topsheet 24 is treated with a masking facilitating agent, as described above.

The topsheet 24 comprises a slit opening 30, along the longitudinal axis x of the diaper 20, which is configured to receive fecal exudates and isolate at least a portion of the exudates from the skin of the wearer.

The topsheet 24 may be fully or partially elasticated. In FIG. 1, the topsheet 24 is partially elasticated by the provision of elastic bands 31 and 32, which have an X-shape.

The slit opening 30 is located in the topsheet 24 such that the fecal exudates pass through the opening into a void space formed between the topsheet 24 and the absorbent core 28 and/or other underlying layers such as preferably an additional sheet which traps the BM, as described above, which preferably has fibers in bonded and unbonded regions, whereby the bonded regions form a planar support structure for the unbonded regions, which serve to trap the BM which has passed through the slit opening 30. Once the BM is in the void space, the specific topsheet 24 of the diaper 20 of the invention ensures that the (majority) of the BM is not visible for the user or caretaker, when changing the diaper 20, and it ensures that BM leakage (e.g. back through the topsheet) is reduced.

The slit opening 30 in the topsheet 24 is located in alignment with the wearer's anus during use. Preferably, the slit opening 30 in the topsheet 24 is located in a target zone of the diaper. The target zone is that portion of the diaper, which is configured to directly receive the insult of fecal matter from the wearer and is generally located in the crotch portion of the diaper. Particularly, in one non-limiting embodiment, the target zone may extend from about 5 to about 30 centimeters in length along the longitudinal axis x of the diaper with about one fourth of its length extending longitudinally from the lateral axis y of the diaper 20 towards the first or front waist region 36 and the remainder extending longitudinally towards the second or back waist region 38, when measurements are made with the topsheet in a fully extended or stretched state. Generally, about 0% to about 40%, preferably 10% to 35% or even 20% to 30% of the slit opening 30 may be located forward of the lateral centerline on the diaper 20.

The slit opening 30 in the topsheet 24 is generally disposed in the target zone along the longitudinal axis x and is defined by two opposing longitudinally extending side edges 40, a front edge 41 and a back edge 42. The front edge 41 is generally located in the crotch region 37 of the diaper 20 towards the first, front region 36, or in the first waist region 36 itself, while the back edge 42 is located in the crotch region 37 near the second waist region 38, or in the second waist region 38 itself. The slit opening 30 includes a length in the longitudinal direction parallel to the longitudinal axis x of the diaper and a width in the lateral direction which is parallel to the lateral axis y of the diaper 20. The length of the slit opening 30 is within the ranges specified above.

The diaper 20 preferably also includes a fastening system, typically including at least one engaging component (or fastener of male fastening component) 27 and at least one landing zone 29 (female fastening component), such as hook-loop type fastening systems. The diaper 20 may also include such other features as are known in the art, including leg cuffs, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092.

The elastic regions 31 and 32 ensure that the opening 30 of the diaper 20 is positioned and remains positioned in the gluteal groove of the buttocks, including the perianal region.

The edge 40 of the slit opening may be held against the wearer ('s skin) allowing the feces to penetrate the slit opening 30 without deflection, via only the elastic forces supplied by the elastic regions 31 and 32, or optionally additionally by use of a body adhering composition, as described above. In any case, it is preferred that the body adhering composition permit vapors to pass (i.e., breathable), be compatible with the skin and otherwise skin friendly. It may also be preferred that the elastic regions 31 and 32 comprise a lotion, or preferably talc or wax, to reduce pressure marks of the elastic regions 31 and 32 on the skin of the wearer. The elasticated regions 31, 32 may be formed by bonding pre-stretched elastic bands along the longitudinal edges 40 of the slit opening 30.

Figure 2:
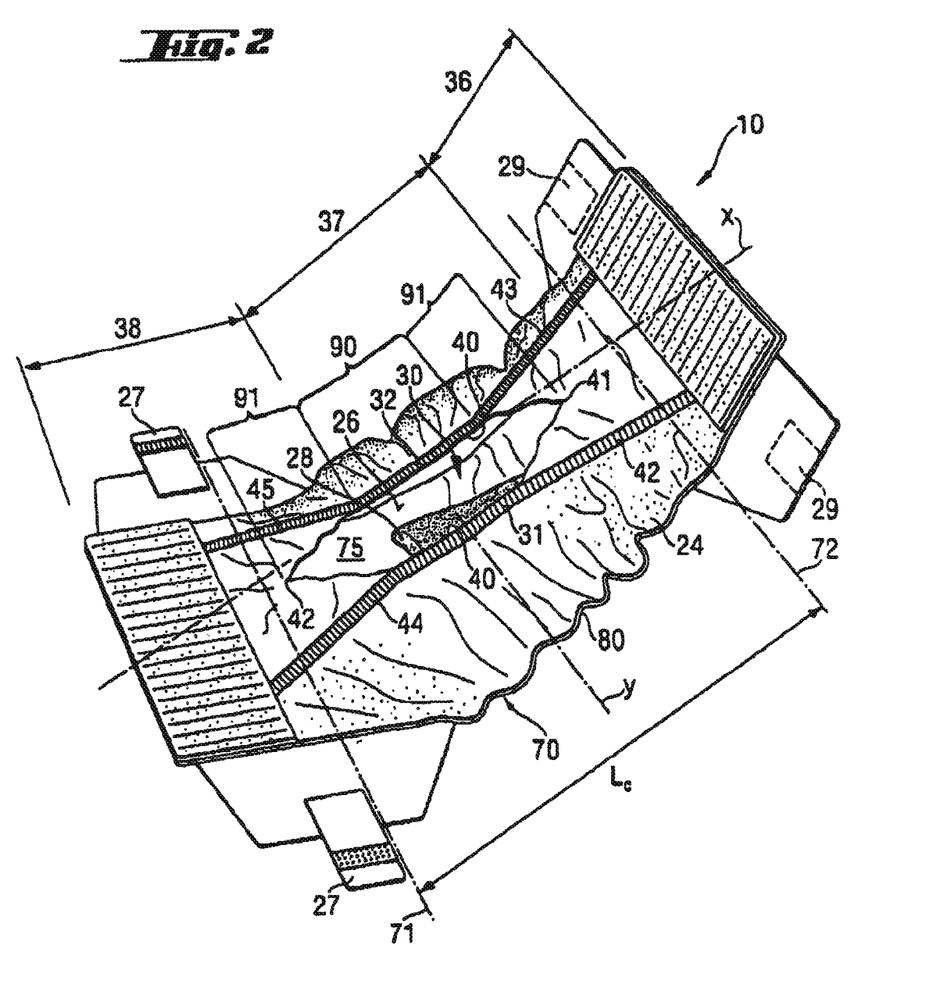
FIG. 2 shows a perspective view of a preferred diaper of the present invention, and the preferred topsheet 24 thereof.

It may be preferred that the article has a slit opening which has a hexagonal shape, as can be seen in FIG. 2, which shows a perspective view of a preferred diaper 20 of the invention. The slit opening 30 contains a rectangular portion 90 and two triangular portions 91 at each side thereof. The length of the slit opening 30 is then measured from the joining point of the edges of the opening 30, in the top of the triangulars 91 (i.e. the length of the longest dimension/longitudinal axis of the hexagonal slit opening 30) and has the preferred values are as specified herein. The width of the hexagonal slit opening 30 is then the width of the transverse axis of this slit 30, orthogonal to the longitudinal axis of the slit opening 30.

The diaper 20 may also have leg cuffs 80 on both longitudinal edges of the diaper 20, typically attached to the backsheet 26. Preferred is that the longitudinal edge of a leg cuff 80, the longitudinal edge of the topsheet 24 and the longitudinal edge of the backsheet 26 are attached together in the form of a thin, longitudinal attachment edge.

What is claimed is:

1. An absorbent article having a longitudinal axis and a lateral axis, the absorbent article comprising:
    a backsheet;
    a topsheet including an inner surface and an outer surface, wherein the inner surface faces the backsheet and wherein the outer surface is disposed opposite the outer surface;
    a means for receiving bodily exudates positioned between the topsheet and the backsheet;
    a slit opening in the topsheet and disposed along the longitudinal axis, wherein the slit opening is configured to allow bodily exudates to pass through the slit opening to the means for receiving bodily exudates;
    wherein said topsheet further comprises a sheet of fibrous material having pores with a uniform pore size distribution and with a maximum pore size of less than 100 μm; and
    wherein the slit opening is unobstructed by the sheet of fibrous material, and wherein the topsheet has an air-permeability of at least 3 Darcy/mm, and wherein the topsheet has an alcohol repellency of at least 7.0.

2. The absorbent article of claim 1, wherein said topsheet has a BM rewet value of less than 4.5 g.

3. The absorbent article of claim 1, wherein the topsheet has a basis weight of less than 40 g/m² and comprises a meltblown non-woven web.

4. The absorbent article of claim 1, wherein the pores of the topsheet have a mean pore size of less than 20 μm.

5. The absorbent article of claim 1, wherein the topsheet comprises a laminate of one or more spunbonded webs and one or more meltblown webs or one or more meltblown webs and one or more carded webs.

6. The absorbent article of claim 1, wherein the topsheet comprises a masking facilitating agent selected from fluorocarbon compounds or siloxane compounds.

7. The absorbent article of claim 1, wherein the slit opening has longitudinally opposing side edges, and one or more elasticated regions disposed along each of the side edges wherein the elasticated regions are longer than the side edges of the slit opening, extending longitudinally from said side edges, each elasticated region having one or more longitudinal extending elastic bands.

8. The absorbent article of claim 7, wherein the elasticated regions or a part thereof that faces the wearer's body in use, comprises a friction reducing agent.

9. The absorbent article of claim 8, wherein the friction reducing agent is a lotion or powder which comprises a talc.

10. The absorbent article of claim 8, wherein the friction reducing agent is a lotion or powder which comprises a wax.

11. The absorbent article of claim 1, further comprising an additional sheet, positioned between the topsheet and the backsheet, being a three-dimensional web of fibres, having a width, length and thickness (caliper) dimension, the web having bonded regions, where the fibers are bonded to one another, and unbonded regions, where the fibers are unbonded to one another, wherein the fibers extend from at least one bonded region through at least one unbonded region to at least one other bonded region and wherein the bonded regions form a support structure for the unbonded regions and the surface area of the unbonded regions is at least 2 mm² and wherein the topsheet has a thickness (caliper) of between 0.1 and 5 mm.

12. The absorbent article of claim 1, wherein the disposable absorbent article is a diaper or training pants.

13. The absorbent article of claims 1, wherein the topsheet has an air permeability of at least 10 Darcy/mm and an alcohol repellency of at least 9.

14. The absorbent article of claim 1, wherein the topsheet has an air permeability of at least 10 Darcy/mm and a BM rewet value of less than 3.5 g.

15. The absorbent article of claim 1, wherein the pores of the topsheet have a mean pore size that is less than 17 μm.

16. The absorbent article of claim 1, wherein the pores of the topsheet have a mean pore size that is less than 13 μm.

17. The absorbent article of claim 1, wherein the pores of the topsheet have a mean pore size that is less than 10 μm.

18. The absorbent article of claim 1, wherein the topsheet has an air permeability of at least 20 Darcy/mm and an alcohol repellency of at least 10.

19. The absorbent article of claim 1, wherein the topsheet has an air permeability of at least 10 Darcy/mm and an alcohol repellency of at least 10.

* * * * *